United States Patent [19]

Slovak

[11] Patent Number: 5,058,605
[45] Date of Patent: Oct. 22, 1991

[54] METHOD AND DEVICE FOR THE CONTROLLED LOCAL, NON-INVASIVE APPLICATION OF DC PULSES TO HUMAN AND ANIMAL TISSUES

[75] Inventor: Petr Slovak, Praha, Czechoslovakia

[73] Assignee: Ceske vysoke uceni technicke, Praha, Czechoslovakia

[21] Appl. No.: 483,061

[22] Filed: Feb. 21, 1990

[30] Foreign Application Priority Data

Feb. 22, 1989 [CS] Czechoslovakia ............ PV1132-89

[51] Int. Cl.⁵ .................................... A61N 1/18
[52] U.S. Cl. .................................... 128/783; 128/421; 128/639
[58] Field of Search .................. 128/639, 783, 423 W, 128/419 F, 800

[56] References Cited

U.S. PATENT DOCUMENTS

| | | | |
|---|---|---|---|
| 2,447,127 | 8/1948 | Landauer | 128/800 |
| 4,354,509 | 10/1982 | Strahwald et al. | 128/639 |
| 4,459,988 | 7/1984 | Dugot | 128/419 F |
| 4,600,010 | 7/1986 | Dugot | 128/419 F |
| 4,619,266 | 10/1986 | Hodgson | 128/639 |
| 4,741,347 | 5/1988 | Robert et al. | 128/800 |
| 4,769,881 | 9/1988 | Pedigo et al. | 128/419 R |
| 4,907,601 | 3/1990 | Frick | 128/783 |
| 4,920,981 | 5/1990 | Dervieux | 128/800 |

FOREIGN PATENT DOCUMENTS 158336 10/1985 European Pat. Off. .
231379 3/1986 European Pat. Off. .

Primary Examiner—William E. Kamm
Assistant Examiner—Scott M. Getzow
Attorney, Agent, or Firm—Klein & Vibber

[57] ABSTRACT

The invention relates to a method and a device for the controlled local, non-invasive electrostimulation of human and animal tissues. The device includes a pulse generator 1 generating DC pulses of adjustable frequency and amplitude and two electrodes to be applied to the tissue. One electrode is a large-surface electrode to be fixedly applied to the body, and the other electrode is a multipoint electrode having a plurality of point electrodes provided in a support and electrically isolated from each other, which are designed to be simultaneously and fixedly applied to the treated region and are sequentially provided with DC pulses from the pulse generator by means of switching means, each switching position corresponding to one point electrode or a predetermined group of point electrodes.

The device is optimally suited for the automatic and home application of electrostimulation, particularly for the therapy of chronic diseases of the locomotor system.

19 Claims, 3 Drawing Sheets

METHOD AND DEVICE FOR THE CONTROLLED LOCAL, NON-INVASIVE APPLICATION OF DC PULSES TO HUMAN AND ANIMAL TISSUES

FIELD OF THE INVENTION

The invention relates to a method and a device for the controlled local, non-invasive application of DC pulses to human and animal tissues and particularly for the electrostimulation of the human and animal body in human and veterinary medicine.

BACKGROUND OF THE INVENTION

For the treatment of patients suffering from chronic problems caused by long-term overstressing of soft tissues of the locomotor system or from certain other chronic complaints (ankylosing spondylitis, spondylarthritis) electrotherapy devices have been widely used for a long time which are adapted to be applied by the patient at home for self-therapy. Most of these devices are based on transcutaneous nerve stimulation (TNS machines).

DE-A-31 51 180 and U.S. Pat. No. 4,790,319 describe an electrotherapy device and a corresponding method for the local, non-invasive treatment of tissues by affecting their metabolism by means of DC pulses in the frequency range of 10 Hz to 10 kHz and particularly of 250 Hz to 5 kHz at voltages of up to 25 V, particularly up to 17 V, the average current being limited to a maximum of about 300 $\mu$A. According to this prior art, the DC pulses are applied by means of a large-surface electrode which is fixedly applied to the body in a neutral region and a small, pin-shaped electrode allowing a point-like contact with the skin within the treated region. The state of the tissue at the treated point may be determined objectively by measuring the change of the average value of the current flowing in the patient circuit with time. The response curve of a normal tissue is such that the average current, $I_{av}$, first increases with time and then reaches a saturation value after a very short time interval of a few seconds. An abnormal tissue status may be detected easily because it results in a quite different characteristic of the time dependence of $I_{av}$ which may show several inflection points before reaching a saturation value which is normally lower than the saturation value of a normal tissue, or which decreases after having reached a maximum value. By applying the pin-shaped electrode sequentially in a matrix-like manner to a plurality of points within the treated region the physiological status of the respective tissue may be determined, the application of the DC pulses simultaneously leading to a remarkable improvement of the physiological status of the tissue which may last for a relatively long time period.

The electrobiochemical interactions of the electric current with the structure of the living tissues leads to an increase in the local blood microcirculation, a recession of oedemas in the treated region and to a myorelaxative effect around the treated point. Such devices, however, cannot be applied by the patient himself at home without a special training with respect to the method of treatment because the pin-shaped electrode must be applied in a sequential manner to a plurality of points in the treated region, and especially with respect to the interpretation of the readings of the current measuring instrument. The time interval necessary for the preparation (fixation of electrodes) and the treatment itself usually lasts more than 10 or 20 minutes. Furthermore, devices for continuous electrostimulation to be worn by the patient may cause severe problems due to allergic reactions of the skin under the electrodes and possible electrolytic deterioration of tissues. Because of these deficiencies, these devices are often used only for a very short period of time which may result in a further development of the disease.

It is the object of the present invention to provide a method and an apparatus for the controlled local, non-invasive application of DC pulses to human and animal tissues which are particularly suited for the electrostimulation of the human and animal body and facilitate the multipoint treatment of the treated region by use of a specific design of the electronic circuitry between the pulse generator and the electrodes, and a specific design of the electrode to be applied to the treated region.

SUMMARY OF THE INVENTION

The method of the present invention for the controlled local, non-invasive application of DC pulses to human and animal tissues and particularly for the electrostimulation of the human and animal body, with exclusion of a diagnostical and therapeutical treatment of the human and animal body, comprises the steps of applying DC pulses of adjustable frequency and amplitude generated by a pulse generator to the tissue or the body by means of two electrodes, one electrode being a large-surface electrode which is fixedly applied to the tissue or the body, and the other electrode comprising a tip and being brought into a point-like contact with the treated region with sequential local application, and controlling the duration $t_{loc}$ of the local application of the DC pulses by means of the electrode on the basis of a predetermined time or the development of the detected level of the average current value $I_{av}$ of the current flowing in the electrode circuit with time in such a manner that the application of the DC pulses is terminated when the average current value $I_{av}$ exceeds a predetermined threshold value and/or when the differential quotient $dI_{av}/dt$ sinks below a predetermined value, and/or when a predetermined time interval beginning with the start of the DC pulse application to the respective electrode is lapsed;

it is characterized in that (a) a multipoint electrode is used comprising a plurality of point electrodes provided in a support and being electrically isolated from each other, which are simultaneously and fixedly applied to the treated region, and (b) the point electrodes or groups of point electrodes of the multipoint electrode are sequentially connected to the respective output of the pulse generator for the controlled duration $t_{loc}$.

In accordance therewith, the point electrodes are sequentially operated by application of DC pulses, and the duration $t_{loc}$ of pulse application is determined and controlled in a sequential manner for each of the operated point electrodes 3'. In dependence of the selected treatment program, each of the point electrodes or point electrode groups may be operated only once or for a predetermined number of cycles.

The shape of the DC pulses may be, for instance, sawtooth-like, triangular or rectangular, the rectangular pulse-shape being preferred. The frequency is preferably selected within the range of 10 Hz to 10 kHz and preferably within the range of 250 Hz to 5 kHz. The pulse width is preferably from 50 to 250 μs and most preferably about 100 μs. The voltage amplitude of the DC pulses may be up to 25 V and preferably up to 17 V.

The DC pulses may be applied continuously or in the form of pulse trains.

The device according to the present invention which is particularly suited for carrying out the above-defined method comprises:

A pulse generator generating DC pulses of adjustable frequency and amplitude, and two electrodes to be applied to the tissue or the body, respectively, one electrode connected to the first output terminal of the pulse generator being a large-surface electrode to be fixedly applied to the tissue or the body, and the other electrode connected to the second output terminal of the pulse generator comprising a tip for point-like contact with the tissue or the body in a treated region and being provided for sequential local application;

it is characterized in that (i) the electrode is a multipoint electrode comprising a plurality of point electrodes provided in a support and being electrically isolated from each other, which are designed to be simultaneously and fixedly applied to the treated region, and (ii) switching means are provided in the output circuit of the pulse generator which are connected to the point electrodes and are designed for sequentially connecting the point electrodes to the second output terminal of the pulse generator, each switching position corresponding to one point electrode or a predetermined group of point electrodes.

In the simplest form, the switching means may be a hand-operated multi-position switch for manually selecting the respective point electrodes, the switching means thus determining the sequence of the sequential switching by the order of the point electrodes connected to subsequent switching contacts.

As an alternative, the switching means may be digitally operated semiconductor switching means, for example of the type as used in telecommunications.

According to a preferred embodiment, the device comprises current detecting means provided in the output circuit of the pulse generator for detecting the average current value $I_{av}$ of the current flowing in the output circuit, a controller for controlling the sequential switching of the switching means, a control unit controlling the controller on the basis of the detected level of the average current value $I_{av}$, the stabilization of the average current value $I_{av}$ with time, the time derivative $dI_{av}/dt$ and/or a predetermined time interval in such a manner that the application of the DC pulses is terminated when the average current value $I_{av}$ exceeds a predetermined, adjustable threshold value and/or when the differential quotient $dI_{av}/dt$ sinks below a predetermined, adjustable value, and/or when the predetermined time interval beginning with the start of the DC pulse application to the respective electrode is over.

In accordance with another preferred embodiment, the control unit comprises a current threshold detector the input of which is connected to the output of the current detecting means and which generates an output signal when the detected average current $I_{av}$ exceeds a predetermined, adjustable limit value, and/or a current stabilization detector the input of which is connected to the output of the current detecting means, and which generates an output signal when the differential quotient $dI_{av}/dt$ sinks below a preset, adjustable limit value, and/or a timer, preferably a voltage controlled timer, which generates an output signal after lapse of a predetermined, adjustable time interval, and a logical circuit, the input of which is connected to the outputs of the current threshold detector, the current stabilization detector and the timer, and the output of which is connected to the input of the controller, thus activating the controller to set the switching means to the next switching position for sequential operation of the point electrodes of the multi-point electrode.

In accordance with another preferred embodiment, the device according to the invention comprises a time analyzer connected to the output of the current detecting means and eventually also to the control unit for analyzing the time dependence of the average current $I_{av}$ and preferably displaying and/or printing the development of $I_{av}$ and/or $dI_{av}/dt$ with time. The time analyzer may further comprise an interface for connecting peripheral devices, for example printers, other displays, acoustical and/or optical signal devices, computer systems etc.

The time analyzer may also comprise a microcomputer system including a rewritable memory device such as a RAM for storing and retrieving operational data of the device, particularly $I_{av}$ and $dI_{av}/dt$ values and their changes with time, for example for comparison of previous treatments of a treated region with later treatment results. The time analyzer may also be designed to display the average current value $I_{av}$ itself, for example by means of a digital or analog measuring instrument.

The controller may comprise a circuit for stopping the DC pulse application by means of the switching means after a predetermined number of switching cycles.

Furthermore, the device may comprise means for changing the polarity of the electrodes. For normal applications and detecting the physiological state of the tissue, the large surface electrode is positive, whereas the needle-shaped electrodes of the multipoint electrode are negative; for producing an analgesic effect, this polarity may be reversed.

The point electrodes of the multipoint electrode may be arranged in a matrix, along a spiral, in zig-zag lines or on concentrical circles, depending on the specific application purpose.

At least the end part of the point electrodes, which may have spring-loaded tips, are of needle-like shape, having a diameter of e.g. about 0.5 to 2.0 mm, and the tips are rounded to avoid any lesion of skin or tissues.

In accordance with a preferred embodiment, the support of the point electrodes of the multipoint electrode is made of a flexible material which allows an elastic deformation to the respective anatomical shape of the treated region. As an alternative, the support may be made of a rigid material and is adapted to a specific anatomical or other desired shape. It may also be made of a rigid material which may be deformed by application of heat for adapting it to a desired shape which then remains fixed.

The stimulation process is terminated when all the treated points were subjected to a predetermined number of pulse applications or stimulations.

The principal advantage of the invention resides in the fact that a treatment of even a rather extended treated region lasts usually less than 1 or 2 minutes, and the application of the current to the point electrodes is controlled electronically on the basis of the response of the treated tissue. Thus the device is suited for self-treatment and home application, and the training of the patient requires only a short instruction. Furthermore, the device is safe in use and enables a simple and comfortable treatment at home, at work or even on travel. No adverse effects on the treated tissue were reported.

BRIEF DESCRIPTION OF THE DRAWINGS

In the following, preferred embodiments of the invention will be described by way of example with reference to the drawings.

FIG. 4a is a schematic illustration of spring loaded electrodes; and

DESCRIPTION OF THE PREFERRED EMBODIMENTS

Figure 1:
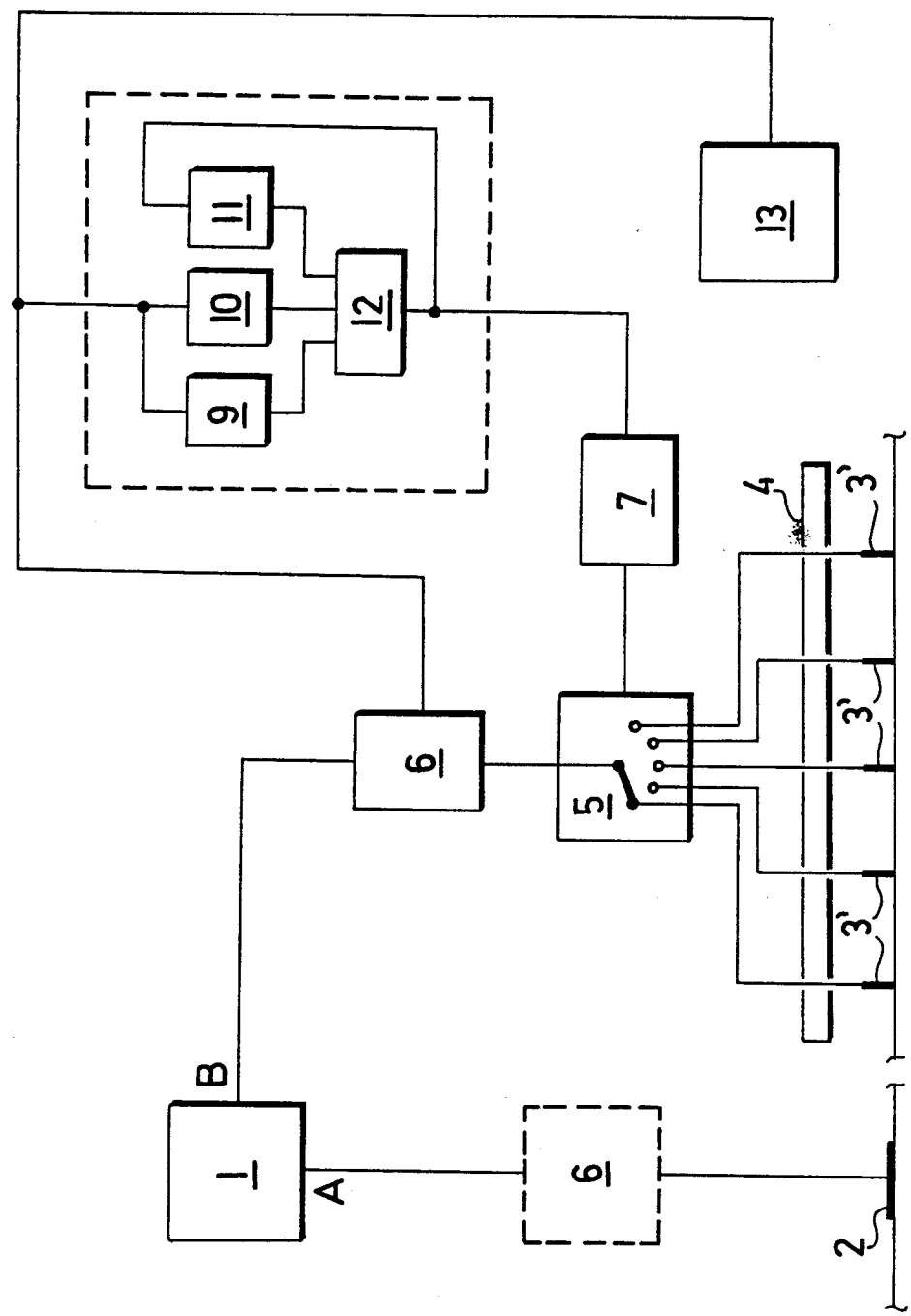
FIG. 1 is a block diagram of a preferred embodiment of the device of the present invention.

The device shown in FIG. 1 comprises a DC pulse generator 1 which is preferably powered by batteries. One output terminal A of the DC pulse generator 1 is connected to a large-surface electrode 2 which is kept in permanent, fixed contact with the tissue or body during treatment in a neutral region 14. This electrode may be applied e.g. to the skin in any suitable region of the body of the patient.

The other output terminal B of the pulse generator 1 is connected through current detecting means 6 to the switching means 5 the switched contacts thereof are connected to the point electrodes 3' of the multipoint electrode 3 which are fixed in a support 4. Alternatively, the current detecting means 6 may also be provided in the line from output terminal A to the large-surface electrode 2 as indicated by the dashed line box.

The current detecting means 6 are preferably a resistor with an RC integrator. The point electrodes 3' are non-invasive and made from an inert electroconductive material such as gold-coated metal or a suitable electrically conductive polymer material. The support 4 may be rigid and plane or may have a form which is anatomically adapted to a treated body region. The support 4 may also be made from an elastic, flexible material such as silicon rubber, which is eventually foamed, or another suitable flexible polymer material, or may be cast from a synthetic resin adapted for medical purposes.

The actual position of the switching means 5 is preferably indicated on a liquid crystal display comprised in the controller 7 the output of which is connected to the switching means 5 and which controls the sequential switching thereof. The liquid crystal display shows the number of the actually treated point. The controller 7 may also comprise a circuit for stopping the pulse application after a predetermined number of switching cycles.

The output of the current detecting means 6 is connected to the input of a control unit 8 which controls the controller 7 and comprises a current threshold detector 9 the input of which is connected to the output of the current detecting means 6 and which generates an output signal when the detected average current $I_{av}$ exceeds a predetermined, adjustable limit value which is selected according to the specific application, a current stabilization detector 10 the input of which is connected to the output of the current detecting means 6 and which generates an output signal when the differential quotient $dI_{av}/dt$, i.e. the time derivative of the average current, sinks below a preset, adjustable limit value. The detection of the average current $I_{av}$ is preferably carried out by means of detecting a corresponding voltage for example corresponding to the voltage drop at a resistor, and accordingly, the current threshold detector 9 may be designed to generate an output signal when the corresponding input voltage exceeds a predetermined limit value, and the current stabilization detector 10 may be designed such that it generates an output signal when the corresponding differential quotient $dV/dt$ corresponding to the differential quotient $dI_{av}/dt$ sinks below the preset limit value. The control unit 8 further comprises a timer 11 which is preferably a voltage controlled timer triggered by the changes in the input voltage.

The logical outputs of the above-mentioned three circuits 9, 10 and 11 are connected to the inputs of a logical circuit 12. The output signal of the logical circuit 12 activates the controller 7 which sets the switching means 5 to the next position according to the switching sequence. The switching sequence may be determined by the structure of the switching means 5 or by a corresponding selection program of the controller 7.

The logical circuit 12 is generally an AND-OR gate circuit.

The provision of the current threshold detector 9 and the current stabilization detector 10 is not always necessary; for specific applications only the timer 11 may be sufficient. In this case, the logical circuit 12 may be a single-input gate or switching means. According to other specific applications, the control unit 8 may comprise only the current threshold detector 9; also in this case, the logical circuit 12 is a single input gate or an analog circuit. In the case of the provision of two of the circuits 9, 10 and 11 the logical circuit 12 is of the OR type. The simple version comprising only a voltage controlled timer 11 is particularly suitable for non-medical applications.

For the practical realization, switching means comprising a stepper motor may be used. Such switching means are suitable for short pulses of high amplitude. In usual applications a CMOS multiplexer switch is also quite satisfactory, with the pulse generator 1 set to a frequency of about 4 kHz, a pulse width of 100 $\mu$s and an amplitude of up to 25 V.

The practical application of this device comprises applying the support 4 comprising the point electrodes 3' of the multipoint electrode 3 to the treated region 15 of the patient's body or an isolated tissue or another biological or biochemical material and applying the large-surface electrode 2 to another suitable region 14, e.g. by simply holding it in the hand. The process of the treatment then starts, proceeds and stops automatically. The average current curves in dependence on the time are recorded and/or displayed by the time analyzer 13.

It is supposed that the point electrodes 3' are brought into contact with the pores of sweat glands on the surface of the treated region 15 in the case of a body treatment. The current applied to the respective point electrodes 3' induces a pulse-like attraction of free ions in the vicinity of the point electrodes 3' and stimulates also the autonomous innervation of the glands. Thus it is possible to influence through the membrane of the sweat gland tissue cells, nerve fibers, blood capillaries and the lymphatic drainage in the area around the stimulated points on the surface of the treated region 15.

The switching means 5 are controlled by the output signal from the current detecting means 6 evaluated in the control unit 8 comprising the current threshold detector 9, the current stabilization detector 10 and the voltage controlled timer 11. The limit value of the current threshold detector 9 may be set individually according to the specific application. It generates an output signal when the detected average current $I_{av}$ exceeds this preset limit value. The current stabilization detector 10 issues an output signal for switching to the next switching position after stabilization of the average current value of the current flowing through the patient circuit when the time derivative $dI_{av}/dt$ sinks below a preset limit value corresponding to the situation that all the free ions around the treated point have been drawn into the ion flow.

The voltage controlled timer 11 ensures switching of the switching means 5 in case of a bad contact of the point electrodes 3' with the surface of the tissue to be treated or in cases of keratinized skin or reflectorily contracted sweat gland pores.

The changes of the average current $I_{av}$ with time reflect the metabolic state of the tissue around the point electrodes 3'. The stimulation in one point takes usually not more than 4 s so that for example 16 points may be treated in 64 s, without changing the overall position of the multipoint electrode 3. The threshold value of the current threshold detector 9 must be set individually for each application, the actual value being derived from values determined experimentally during stimulation of the treated tissue region.

The geometrical arrangement of the point electrodes 3' in the multipoint electrode 3 is preferably adapted to the treated anatomical structures, for example to the lymphatic and nerve paths, muscle groups etc.

The time analyzer 13 may also comprise a display such as a liquid crystal display or a computer terminal comprising an A/D converter card. The time analyzer is then used for observation of the dynamics of the changes in the treated region and also for the adjustment and checking of the device for controlled local electrostimulation and pulse treatment of tissues.

Figure 2:
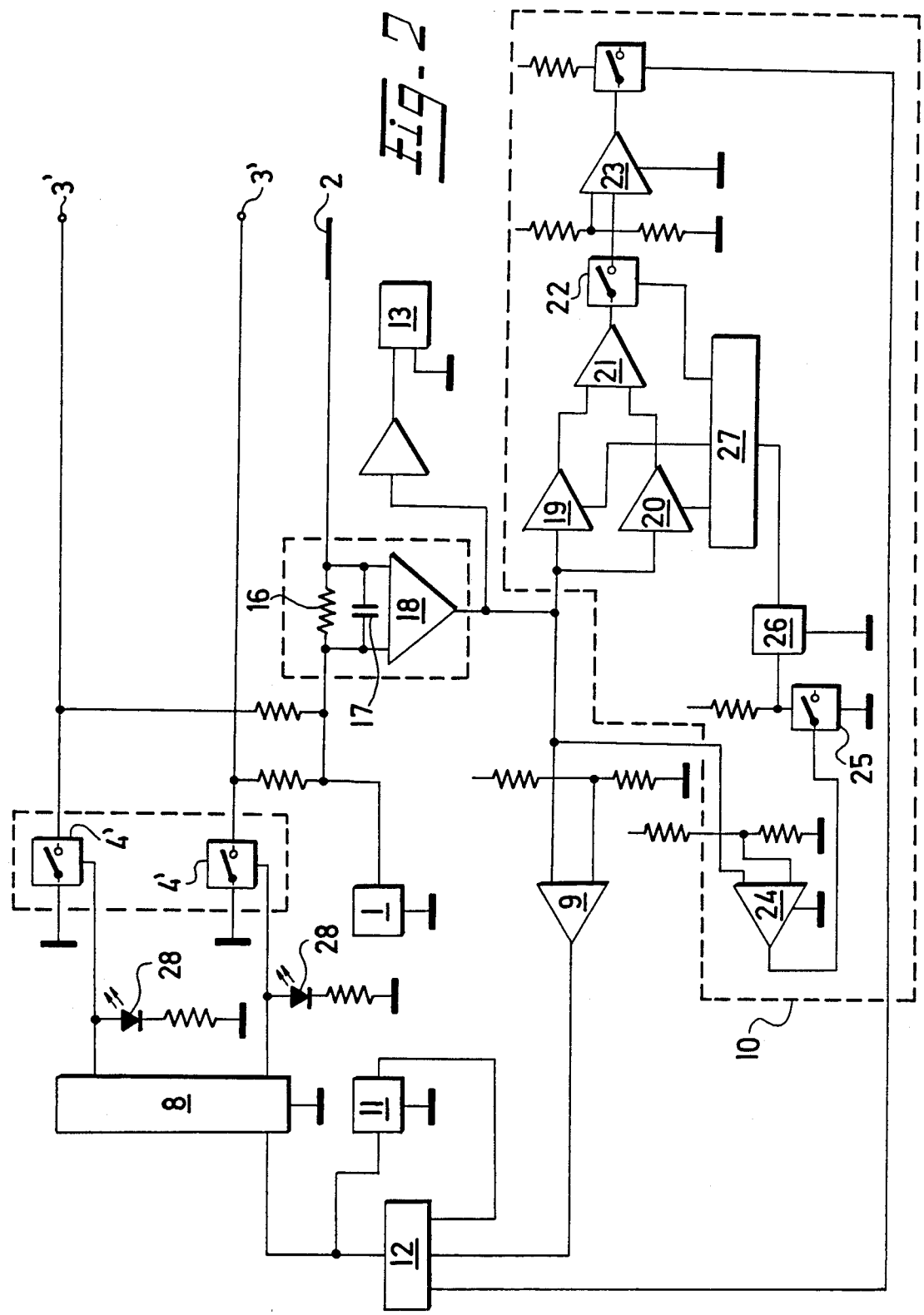
FIG. 2 is a circuit diagram corresponding to the embodiment of FIG. 1.

The circuit shown in FIG. 2 is a schematic representation of the embodiment shown in FIG. 1. The DC pulse generator 1 is connected to switching means 5 comprising a number of integrated analog switches 5' controlled by the control unit 8 consisting of a ring counter with an integrated digital multiplexer. Thus, the pulses from the output of the pulse generator 1 are sequentially applied to the respective point electrodes 3', the progress of the stimulation or the sequence of switching preferably being indicated by LEDs 28. The patient current flowing through the output circuit of the pulse generator 1 is detected in the line the to the large-surface electrode 2 by means of current detecting means 6 comprising a RC filter circuit consisting of a resistor 16 and a capacitor 17, and a differential amplifier 18. The output voltage of the differential amplifier 18 corresponds to the average value of the patient current $I_{av}$.

The output of the differential amplifier 18 is connected to the input of the current threshold detector 9 consisting of a simple voltage comparator and also to the input of the current stabilization detector 10. The input of the current stabilization detector 10 comprises two sample-and-hold analog circuits 19 and 20, the outputs of which are connected to the inputs of a differential amplifier 21. The output of this amplifier is connected via an analog switch 22 to the output of a voltage comparator 23. The sample-and-hold circuits 19 and 20 together with the switch 22 are controlled by signals from different outputs of a digital ring counter 27 which in turn is controlled by a clock generator 26. The clock generator 26 is switched on and off by switch 25 controlled by the signal of a voltage comparator 24.

The output of the differential amplifier 18 is further connected to the time analyzer 13.

Thus, a certain minimal value of the signal at the output of the current detecting means 6 starts the clock generator 26 controlling the ring counter 27. The sample-and-hold circuits 19 and 20 start sampling the input voltage at different times corresponding to the activation of the respective outputs of the ring counter 27. The signals at the outputs of the sample-and-hold circuits are subtracted in a differential amplifier 21. The value of the voltage at its output corresponds to the time derivative $dI_{av}/dt$ of the patient current $I_{av}$. This voltage is, in the next step of the counting cycle of the ring counter 27, applied to the input of a voltage comparator 23 by means of the switch 22, the voltage comparator 23 detecting whether its input signal drops below a preset minimum value.

The logical signals from the current threshold detector 9 and the current stabilization detector 10 are applied to the inputs of the logical circuit 12 consisting of a logical gate. The timer 11 is connected between the output and one of the inputs of this circuit. Thus, if the logical circuit 12 does not receive any signal after a certain time both from the current threshold detector 9 and the current stabilization detector 10, its output is set to high value by the timer 11. The signal from the output of the logical circuit 12 sets the controller 7 to the next count and thus selects the next point electrode 3' for pulse application.

Figure 3:
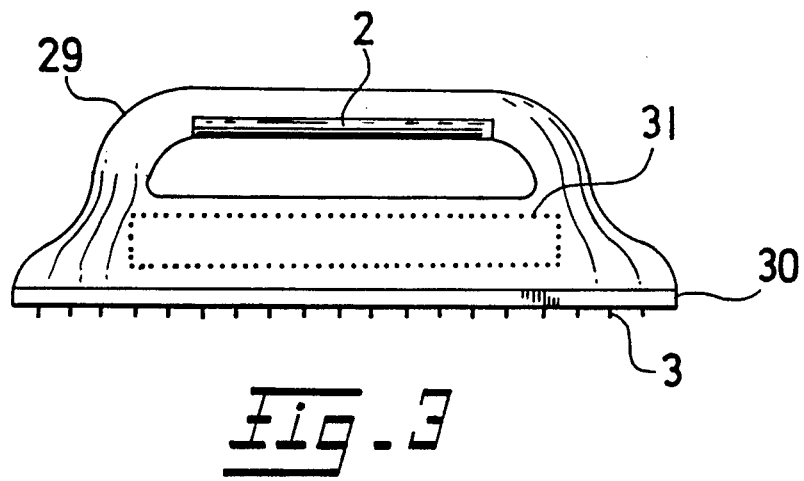
FIG. 3 shows a preferred design of the device according to the present invention in the form of a single-piece hand-held device.

FIG. 3 shows a very advantageous embodiment of the device according to the present invention which is designed as one single piece comprising a handle-like part 29 with integrated large-surface electrode 2 and a bottom part 30 comprising the point electrodes 3' of the multi-point electrode 3 provided in a support. The device comprises all electronic parts 31 schematically indicated with dashed lines. This device also comprises the electrical power source in the form of batteries, and a switch for starting and stopping the operation. It may also comprise a liquid crystal display for indicating $I_{av}$, $dI_{av}/dt$, etc. This single-piece device is optimally suited for self and home treatment or for other standard applications.

Figure 4:
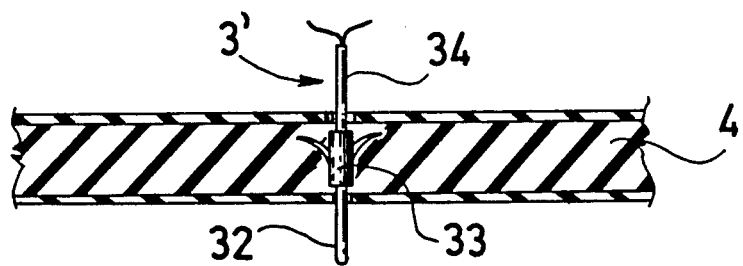
FIG. 4 shows an embodiment of the fixation of point electrodes in a support.

FIG. 4 shows the support 4 consisting of a sandwich-like structure of a rigid or flexible polymer material comprising an inner region in which the point electrodes 3' are fixed by means of a dowel-like clamp 33. A flexible support 4 allows an easy adaptation of the multipoint electrode to the anatomical shape of the treated region. The point electrodes 3' comprise a connecting shaft 34 and a rounded point tip 32 which is preferably spring-loaded, particularly when the support 4 is rigid.

Figure 5:
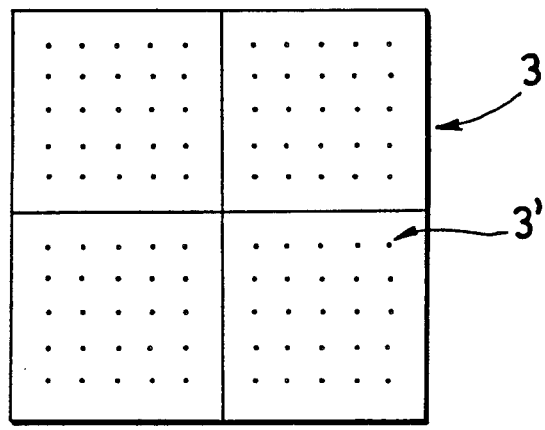
FIG. 5 shows the principle of the subdivision of the multipoint electrode into a plurality of point electrode groups which may be operated independently.

FIG. 5 schematically shows the area of a multipoint electrode 3 which is subdivided into four point electrode groups I to IV, each point electrode group comprising a plurality of point electrodes 3' as indicated in the field of group I. The point electrodes of the point electrode groups I to IV are preferably operated independently by a combination of a switching device 5, current detecting means 6, a controller 7 and a control unit 8 allotted to the respective point electrode groups; alternatively, also a sequential operation of the point electrode groups with use of aonly one electrical system is also possible. According to a preferred embodiment, the time analyzer 13 (FIGS. 1 and 2) is designed in the case of a subdivision of the multipoint electrode into a plurality of point electrode groups in such a manner that it may display the respective operational parameters independently for the different point electrode groups.

The device according to the invention was successfully used in patients with more than 10 years history of chronic arthritits. The support 4 was shaped individually to the form of the patients' knees. Eight point electrodes were arranged along the blood vessel paths in the treated region. The patients applied the device usually four or five times a week. The process of the stimulation was not longer than approximately 50 s. The patients reported recession of pain and tension in the knee region. Objective findings have shown a better mobility and a lower demand for accompanying analgesics.

In patients with long-term ankylosing spondylitis, the supports were shaped to the form of the spine. In some cases three eight-electrode systems were used at the same time. The electrodes were arranged in four parallel lines along the spine and in certain cases in spirals around the ankylosing vertebrae. The patients have been applying such an apparatus in the mornings about three times a week. The treatment lasted about 80 s. The electrode systems were fastened to the wall, and the patients simply leaned against them. The patients reported lowering of the tension in the paravertebral region. Objective findings have shown that there were lower demands for drugs and a better mobility.

The concept of the present invention may also be applied to non-medical applications. Very interesting results were achieved when applying the device according to the invention in the field of quality control of meat and meat products. In this case, a number of point electrodes 3' fixed in a support 4 is applied to a sample, for example a piece of meat or a slice of sausage placed on the large-surface electrode 2. The average current curves with time are recorded and displayed by means of the time analyzer 13. Experiments have shown that the average current vs. time curves reflect, apart from the salt content, local pH, water content and other parameters, also the changes corresponding to the ripening and ageing of the products. Accordingly, such a device may be used advantageously for the automatic quality control of meat products.

The device according to the present invention represents a suitable complement to the usual physiotherapeutic methods for the treatment of chronic diseases of the locomotor system, especially in old people and under home conditions. It may be applied also for the diagnosis of non-living cell systems such as meat and other food products. Other preferable applications are the electro-stimulation of tissues or organs provided for organ transplantation, and the use for sport and fitness training purposes, for tests of physiological and fitness conditions, and for aptitude tests.

What is claimed is:

1. In a method for the controlled local non-invasive application of DC pulses to human and animal tissue where pulses are generated by a pulse generator and applied by means of two electrodes, a fixed large surface electrode and a movable point electrode, where the point electrode is moved from one point to another after a controlled duration, the improvement comprising
    said DC pulses being rectangular pulses having a frequency of from 10 Hz to 10 kHz, a pulse width of from 50 $\mu$s to 250 $\mu$s and a amplitude less than or equal to 25 V;
    substituting a multipoint electrode for said point electrode, said multipoint electrode comprising a plurality of point electrodes mounted in a support and being electrically isolated from each other;
    applying said multipoint electrode so that substantially all of said plurality of point electrodes simultaneously contact a treated region;
    providing switching means in series between said pulse generator and said multipoint electrode so that one or more of said plurality of point electrodes are sequentially selectable for connection to said pulse generator;
    switching said switching means according to a controlled duration.

2. The method as claimed in claim 1 wherein said controlled duration is a predetermined number of pulse cycles.

3. The method as claimed in claim 1 wherein said controlled duration is derived from a measurement of current flowing through the electrodes.

4. The method as claimed in claim 1 further comprising the steps of providing display means for indicating the point electrodes connected to said pulse generator and for indicating said controlled duration.

5. The method as claimed in claim 1 further comprising the steps of repeating the sequential connection of said point electrodes to said pulse generator for a predetermined number of cycles.

6. An apparatus for the controlled local non-invasive application of DC pulses to human and animal tissues comprising
    a DC pulse generator generating rectangular pulses having a frequency of from 10 Hz to 10 kHz, a pulse width of from 50 $\mu$s to 250 $\mu$s and an amplitude less than or equal to 25 V;
    a relatively large surface fixed electrode electrically connected to said generator;
    a movable multipoint electrode comprising a plurality of point electrodes mounted in a support, said point electrodes being electrically isolated from each other;
    switching means for connecting said multipoint electrode to said generator whereby one or more of said point electrodes may be sequentially connected to said generator.

7. An apparatus as claimed in claim 6 wherein the plurality of point electrodes are mounted in said support in a geometric pattern.

8. An apparatus as claimed in claim 6 wherein the plurality of point electrodes are mounted in said support by spring loading.

9. An apparatus as claimed in claim 6 wherein said support of said plurality of point electrodes is anatomically shaped to fit a treated region.

10. An apparatus as claimed in claim 6 wherein said support of said plurality of point electrodes is flexible so that it can be anatomically shaped to fit a treated region.

11. An apparatus as claimed in claim 6 wherein the apparatus is constructed within a single hand holdable housing, a hand holdable part of said housing forming said large surface electrode and an opposite part of said housing forming said multipoint electrode.

12. An apparatus as claimed in claim 6 wherein said plurality of electrodes are arranged in groups and connected by said switching means to said generator in said groups.

13. An apparatus as claimed in claim 6 further comprising
control means connected to said switching means for activating said switching means in response to a control signal.

14. An apparatus as claimed in claim 13 wherein said control means includes a timer.

15. An apparatus as claimed in claim 13 further comprising
current sensing means connected to said generator for detecting the value of current flowing through said electrodes;
said current sensing means being connected to said control means whereby said switching means is activated in response to said current sensing means.

16. An apparatus as claimed in claim 15 wherein said current sensing means further comprises
means for determining average current over time and means for determining the time derivative of average current.

17. An apparatus as claimed in claim 15 wherein said current sensing means further comprises
means for determining average current over time and means for determining current threshold.

18. An apparatus as claimed in claim 15 further comprising
said current sensing means further comprises means for determining threshold current and means for determining current stabilization;
a timer and a logical gate, said gate being arranged in series between said control means at the output of said gate and said timer, said means for determining threshold current and said means for determining current stabilization being connected to the input of said gate.

19. An apparatus as claimed in claim 15 further comprising
display means for indicating the status of said current sensing means and said control means.

* * * * *